(12) United States Patent
Hall et al.

(10) Patent No.: US 9,437,041 B2
(45) Date of Patent: Sep. 6, 2016

(54) 3D LASER ABLATION TOMOGRAPHY

(71) Applicant: The Penn State Research Foundation, University Park, PA (US)

(72) Inventors: Benjamin Hall, State College, PA (US); Jonathan Lynch, Boalsburg, PA (US); Edward W. Reutzel, State College, PA (US); Galen Lynch, Cambridge, MA (US)

(73) Assignee: The Penn State Research Foundation, University Park, PA (US)

( * ) Notice: Subject to any disclaimer, the term of this patent is extended or adjusted under 35 U.S.C. 154(b) by 75 days.

(21) Appl. No.: 14/067,502

(22) Filed: Oct. 30, 2013

(65) Prior Publication Data

US 2014/0247443 A1 Sep. 4, 2014

Related U.S. Application Data

(60) Provisional application No. 61/720,144, filed on Oct. 30, 2012.

(51) Int. Cl.
| | |
|---|---|
| *G01N 1/00* | (2006.01) |
| *G06T 17/00* | (2006.01) |
| *G01N 1/06* | (2006.01) |
| *G01N 1/04* | (2006.01) |
| *G01N 1/28* | (2006.01) |

(52) U.S. Cl.
CPC ............ *G06T 17/00* (2013.01); *G01N 1/06* (2013.01); *G01N 2001/045* (2013.01); *G01N 2001/2886* (2013.01); *G06T 2200/08* (2013.01)

(58) Field of Classification Search
CPC .... G06T 11/003; G01N 21/718; G01N 1/06; G01N 2001/045
See application file for complete search history.

(56) References Cited

U.S. PATENT DOCUMENTS

| | | | | |
|---|---|---|---|---|
| 7,133,137 | B2 * | 11/2006 | Shimmick | A61B 3/1005 356/479 |
| 7,535,565 | B1 * | 5/2009 | Viertl et al. | 356/318 |
| 2001/0016736 | A1 | 8/2001 | Lin | |
| 2009/0204110 | A1 | 8/2009 | Islam | |

FOREIGN PATENT DOCUMENTS

| | | |
|---|---|---|
| WO | WO-03060477 | 7/2003 |
| WO | WO-2006037236 | 4/2006 |

OTHER PUBLICATIONS

Mateo et al., "Surface interaction and chemical imaging in plasma spectrometry induced with a line-focused laser beam", 2002, Elsevier, Spectrochimica Acta Part B, pp. 601-608.*
Mateo et al., "Chemical Imaging Using Microline Laser Ablation: Performance Comparison of Gaussian and Flat Top Lasers", 2003, Applied Spectroscopy, vol. 57, No. 3, pp. 343-348.*

(Continued)

*Primary Examiner* — Michael A Lyons
(74) *Attorney, Agent, or Firm* — Dinsmore & Shohl LLP; Douglas L. Wathen

(57) ABSTRACT

A laser ablation tomography system includes a specimen stage for supporting a specimen. A specimen axis is defined such that a specimen disposed generally on the axis may be imaged. A laser system is operable to produce a laser sheet in a plane intersecting the specimen axis and generally perpendicular thereto. An imaging system is operable to image the area where the laser sheet intersects the specimen axis.

17 Claims, 1 Drawing Sheet

(56) References Cited

OTHER PUBLICATIONS

Targowski P., et al., "Picosecond Laser Ablation System with Process Control by Optical Coherence Tomography," Proc of SPIE 7391, pp. 7391-15, 2009, par. 2.2-2.4.

Fujimoto J., et al., "Optical Coherence Tomography: An Emerging Technology for Biomedical Imaging and Optical Biopsy," Neoplasia, 2(1-2):9-25, par. Guiding Surgical Intervention, Jan. 2000.

International Search Report and Written Opinion for PCT/US2013/067438 dated Feb. 13, 2014.

M.P. Echlin, et al. "A New Femtosecond Laser-Based Tomography Technique for Multiphase Materials," Adv. Mater., 23, pp. 2339-2342, 2011.

Search Report issued in co-pending European application No. 13851579.6 dated Jul. 11, 2016.

* cited by examiner

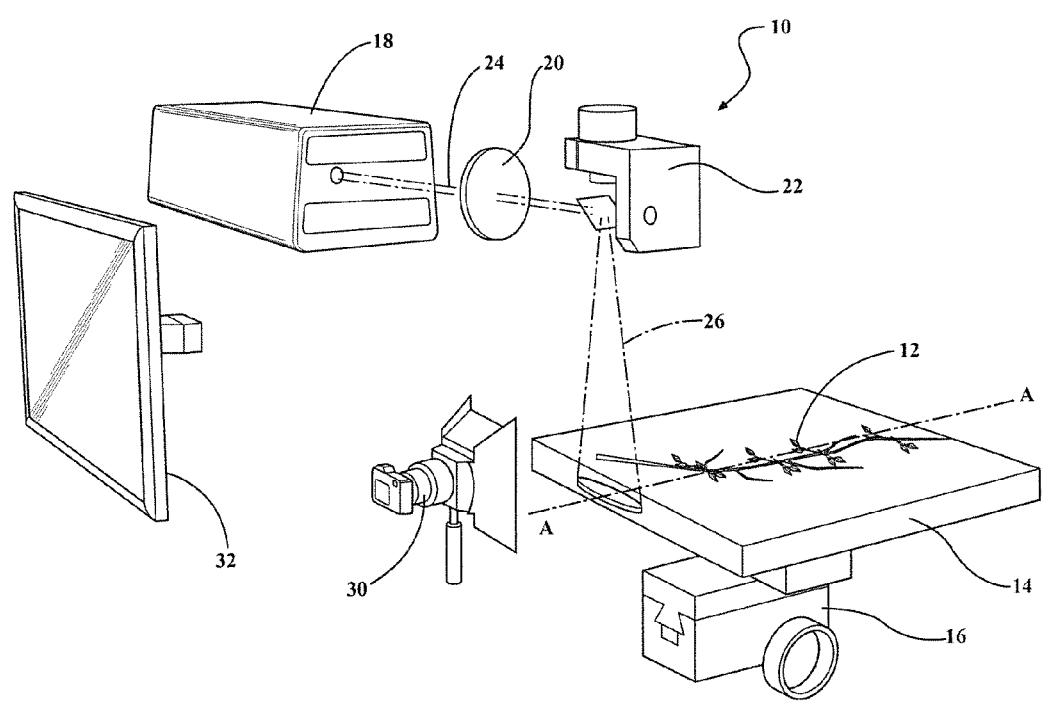

3D LASER ABLATION TOMOGRAPHY

CROSS REFERENCE TO RELATED APPLICATION

This patent application claims priority from U.S. provisional patent application Ser. No. 61/720,144, filed Oct. 30, 2012, the entire content of which is incorporated herein in its entirety.

STATEMENT OF GOVERNMENT SPONSORSHIP

This invention was made with government support under Grant No. IOS0965380, awarded by the National Science Foundation and from the United States Department of Agriculture under Hatch Act Project No. PEN04372. The Government has certain rights in the invention.

STATEMENT OF GOVERNMENT SUPPORT

This invention was made with government support under Grant No. W00014-05-C-0241 awarded by the Office of Naval Research. The government has certain has rights in the invention.

FIELD OF THE INVENTION

The present invention relates generally to imaging methods and apparatus.

BACKGROUND OF THE INVENTION

A commonly practiced non-destructive technique, confocal microscopy, allows for the imaging of thin planes of focus without background noise interference. These images can be stacked to form a three dimensional model of a subject, but is restricted to sub-millimeter regimes and translucent or transparent matter. Another newly developed method of laser tomography described in M. P. Echlin et al., "A New Femtosecond Laser-Based Tomography Technique for Multiphase Materials," *Adv. Mater.*, 23:2339-2342 (2011), uses a beam oriented perpendicularly to the imaged surface, and removes material at known rates. This method is used for metals and would not work well for samples with varying consistency, density, porosity, and absorption coefficients, as the penetration depth would vary depending on these characteristics.

Other means to image specimens include a microtome method and X-ray microtomography. A microtome (similar in concept to a meat slicer) is used to cut thin sections of a specimen embedded in a paraffin wax substrate which then are transferred to a solution bath to remove excess substrate, then transferred to an imaging device, aligned, acquired, and digitally stacked into a 3D model. X-ray tomography is nondestructive and uses virtual slices taken by a thin X-ray beam and computationally reconstructed. However, this method does not yield compositional data or color, and instead produces a map of the materials' X-ray absorptivity (related to a density profile).

SUMMARY OF THE INVENTION

The present invention provides a method for imaging or analysis of the interior structure of a specimen, using a laser sheet or beam that is parallel to the imaging plane. The invention ablates only the desired amount of the specimen by moving a stage.

BRIEF DESCRIPTION OF THE DRAWINGS

FIG. 1 is a perspective schematic of an embodiment of a 3D laser ablation tomography system in accordance with the present invention.

DETAILED DESCRIPTION OF THE INVENTION

The present invention provides a method and apparatus for tomography. It is noted that the term "tomography" often refers to the reconstruction of a specimen through interpretation of the interaction of a "penetrating wave" like X-rays or sound waves within a body. The term "tomography" is used herein to more broadly mean "analysis of interior structure", and will refer to the reconstruction of a selected specimen to produce data similar to conventional tomographic techniques.

Embodiments of the present invention provide a high-speed, automated, high resolution, and inexpensive tomographic technique. A working system has been reduced to practice for the specific case of sectioning and 3D reconstruction of plant roots, among other biological specimens. However, the present invention is useful for analysis of other types of materials and specimens, and the herein described embodiments are not intended to limit the scope of the invention.

According to some embodiments, a specimen is moved through a laser "sheet" which ablates a cross section of the specimen. This cross section is imaged using an imaging system. The movement of the specimen, the laser ablation and the imaging may be done in a continuous process or in incremental steps, as will be described in more detail.

Referring to FIG. 1, an embodiment of a tomographic imaging system is shown generally at 10. The system may be used to analyze a sample or specimen 12, which is illustrated as a piece of plant material. The specimen 12 is supported on a specimen stage 14. The system may be said to have a specimen axis A-A, with the specimen being positioned generally along this axis. The specimen does not necessarily need to have an axis or be positioned such that its longest dimension is along the axis.

In the illustrated embodiment, the stage moves such that the specimen is moved along the specimen axis. Additional movement may also be provided, such as vertical, side-to-side, and or tilting in various ways. A movement system 16 is used for moving the stage 14. This movement may take a variety of forms. While the stage 14 is illustrated as having a flat surface, the stage may take any form useful for supporting a specimen, and may be considered a specimen support.

A laser "sheet" is provided by a laser system. In this embodiment, a short pulsed laser ($<10^{-6}$ seconds, e.g. a nanosecond, picosecond or femtosecond laser) 18 produces a beam 24 that passes through beam shaping optics 20. A beam director 22 rapidly scans a laser beam along a line to create a "plane" of light, thereby providing the laser sheet 26. As shown, the laser sheet 26 is perpendicular to the specimen axis A-A. As such, the laser sheet ablates a "slice" of the specimen as the specimen is moved into the sheet.

Short-pulsed lasers are well-suited for a laser system of the present invention because of their high peak-power (irradiance, measured in W/cm$^2$). This high peak power and short pulse duration induce rapid vaporization, or ablation, of the impinged target material with minimal heat effects. This characteristic allows this method to be used on a wide range of materials.

An imaging system 30 is positioned in alignment with the axis A-A so that the system can image the cross-section of the specimen as it is being ablated. It may also image the specimen before or after ablation, depending on setup of the system. In this embodiment, the imaging system is a magnified Charged Coupled Device (CCD) type camera system, such as a digital SLR camera with a lens focused on the imaging plane defined by the sheet 26. Other types of imaging systems may also be used.

A control system is provided for controlling the imaging device, the stage movement mechanism and the laser system. In the illustrated embodiment, the control system takes the form of a general-purpose computer, represented at 32, modified to perform the control functions.

In this example, reconstruction of a specimen occurs in the following 5 steps:

1. Articulated by mirrors and focusing optics, a rapidly scanned, pulsed laser beam repeatedly sweeps along a line, and creates a planar "sheet of light". The pulse repetition rate of the laser is sufficiently high to allow each subsequent pulse to overlap the prior as the beam sweeps along the line, ensuring a smooth surface.

2. The imaging device with its focus co-planar with the laser sheet records visual data from a specimen on the opposite side of the laser sheet.

3. The stage holding the specimen moves the specimen into the laser sheet, either incrementally or continuously.

4. As the specimen intersects the laser sheet, its camera-facing surface is ablated, exposing the next layer.

5. This laser-sheet has a dual purpose—providing a mechanism by way the surface is both ablated and illuminated. This exposure is useful in that the specimen is illuminated only in a plane, and illuminates evenly regardless of porosity, homogeneity, or material type.

This method rapidly scans a laser beam along a line to create a "plane" of light. A high magnification camera has its focus set to this plane. A mechanical stage holding the object to be processed slowly pushes the specimen through this focal plane, with its camera-facing surface continuously being ablated. Or, alternatively, the specimen can be moved through the focal plane in discrete steps. The camera captures this sequence of surface removal in HD video or still images. Because the laser beam is irradiating and illuminating just the surface, it is the surface that is imaged. This characteristic enables subsequent post-processing and stacking of images with a computer program with minimal re-editing.

Example System:

In one example, a system is used for horticulture specimens using the following components:

A Q-switched, 3rd harmonic, Coherent Avia laser with 30 nanosecond pulses and 355 nanometer wavelength GSI Lumonics scanner Aerotech stages Canon T3i DSLR with a 65 millimeter MP-E 1-5× macro lens ImageJ—software from the National Institute of Health A method in accordance with the present invention can produce high-resolution 3D models of nearly any small specimen that can be ablated with a laser. Laser tomography removes small predefined depths of a surface continuously. By adjusting laser parameters, specimens ranging from extremely delicate to much harder materials can be processed. Both a feather and a silicon wafer have been demonstrated on a prototype system.

Using a picosecond or femtosecond laser may be preferred for the sectioning and 3D reconstruction method of the present invention, as it is well understood that the duration of the pulse is on the same order as the thermal diffusion time for many materials, allowing for ablation with minimal thermal effects. This means that specimens that are delicate, fragile, flammable, or highly sensitive to thermal damage can likely be cleanly sectioned using this process. Additionally, the high irradiance of these pulses means that nearly any material can be ablated and imaged.

The use of a femtosecond or picosecond laser may be preferred for the inventive method. Both investigations and research have shown that there is superior edge quality, reduced thermal impact, increased allowable specimen dimensions (due to higher irradiance and more obtainable ablation thresholds) and wider range of materials that can be processed using ultrafast lasers. Additionally, using shorter wavelengths causes the photons to have bond-breaking energies, which is an athermal process. The use of components like axicon and Fresnel lenses in conjunction with beam-shaping optics can increase the effective depth of field (DOF) and further enhance the process quality.

As will be clear to those of skill in the art, the illustrated and discussed embodiment of the present invention may be altered in various ways without departing from the scope or teaching of the present invention. As one non-limiting example, mirrors may be used to move the imaging device off axis, for packaging or other reasons. It is the following claims, including all equivalents, which define the scope of the invention

We claim:

1. A laser ablation tomography system, comprising:
   a specimen stage for supporting a specimen having a specimen axis defined from a fore end of the specimen to an aft end of the specimen;
   a laser system operable to produce a laser sheet in an imaging plane, wherein the imaging plane intersects the specimen axis and is generally perpendicular thereto, the laser sheet operable to ablate a cross-sectional slice of the specimen at the imaging plane, thereby exposing a cross-sectional surface of the specimen at the imaging plane; and
   an imaging system having a viewing path, the viewing path defined from the imaging plane to the imaging system, the imaging system operable to image the cross-sectional surface of the specimen being ablated during, before and/or after the laser sheet ablates a cross-sectional slice of the specimen.

2. A laser ablation tomography system in accordance with claim 1, wherein the laser system comprises a laser operable to produce a laser beam and a beam director operable to scan the laser beam so as to create the laser sheet.

3. A laser ablation tomography system in accordance with claim 2, wherein the laser system further comprises beam shaping optics disposed such that the beam from the laser passes therethrough.

4. A laser ablation tomography system in accordance with claim 1, further comprising:

a movement system operable to move the specimen stage along the specimen axis.

5. A laser ablation tomography system in accordance with claim 4, further comprising:
a control system operable to control the imaging system and the movement system.

6. A laser ablation tomography system in accordance with claim 1, wherein the imaging system comprises a camera with a Charged Coupled Device (CCD).

7. A laser ablation tomography system in accordance with claim 1, wherein the laser system includes a laser, the laser being a short pulsed laser having pulses with a duration less than $10^{-6}$ seconds.

8. A laser ablation tomography system in accordance with claim 1, wherein:
the specimen stage has a front and an opposing back, the fore end of the specimen being disposed toward the front of the specimen stage and the aft end of the specimen being disposed toward the back of the specimen stage such that the specimen axis extends from the front to the back of the stage; and
the imaging system faces the front of the specimen stage.

9. A method for laser ablation tomography, comprising the steps of:
providing the laser ablation tomography system of claim 1;
positioning a portion of a specimen where the laser sheet intersects the specimen axis;
slicing through the specimen at an imaging plane perpendicular to the specimen axis by ablating the specimen with the laser sheet thereby exposing a cross section surface of the specimen; and
imaging the cross-sectional surface of the specimen during, before and/or after the specimen is sliced.

10. A method of claim 9 further comprising repeating the slicing and imaging steps in increments.

11. A laser ablation tomography system, comprising:
a specimen support for supporting a specimen in a specimen area, the specimen area having a specimen axis defined therethrough, the specimen axis extending from a front to a rear of the specimen area, the specimen having a fore end and an opposing aft end, wherein the fore end of the specimen is disposed toward the front of the specimen area and the aft end of the specimen is disposed toward the rear of the specimen area along the specimen axis;
a laser system operable to produce a laser sheet in an ablation plane, wherein the ablation plane intersects the specimen axis and is generally perpendicular thereto, the laser sheet operable to ablate a cross-sectional slice of the specimen at the ablation plane, thereby exposing a cross-sectional surface of the specimen at the ablation plane; and
an imaging system facing the front of the specimen area, the imaging system having a viewing path, the viewing path defined from the imaging system towards the fore end of the specimen along the specimen axis, the viewing path being generally perpendicular to the ablation plane, the imaging system operable to image the cross-sectional surface of the specimen being sliced ablated from the fore end towards the aft end during, before and/or after the laser sheet ablates a cross-sectional slice of the specimen.

12. A laser ablation tomography system in accordance with claim 11, wherein the laser system comprises a laser operable to produce a laser beam and a beam director operable to scan the laser beam so as to create the laser sheet.

13. A laser ablation tomography system in accordance with claim 12, wherein the laser system further comprises beam shaping optics disposed such that the beam from the laser passes therethrough.

14. A laser ablation tomography system in accordance with claim 11, further comprising:
a movement system operable to move the specimen support along the specimen axis.

15. A laser ablation tomography system in accordance with claim 14, further comprising:
a control system operable to control the imaging system and the movement system.

16. A laser ablation tomography system in accordance with claim 11, wherein the imaging system comprises a camera with a Charged Coupled Device (CCD).

17. A laser ablation tomography system in accordance with claim 11, wherein the laser system includes a laser, the laser being a short pulsed laser having pulses with a duration less than $10^{-6}$ seconds.

* * * * *

UNITED STATES PATENT AND TRADEMARK OFFICE
CERTIFICATE OF CORRECTION

Page 1 of 1

PATENT NO.        : 9,437,041 B2
APPLICATION NO.   : 14/067502
DATED             : September 6, 2016
INVENTOR(S)       : Benjamin Hall et al.

It is certified that error appears in the above-identified patent and that said Letters Patent is hereby corrected as shown below:

Column 1, Line 23: Delete "STATEMENT OF GOVERNMENT SUPPORT"

Column 1, Lines 26-29: Delete "This invention was made with government support under Grant No. W00014-05-C-0241 awarded by the Office of Naval Research. The government has certain has rights in the invention."

Signed and Sealed this
Second Day of May, 2017

Michelle K. Lee
*Director of the United States Patent and Trademark Office*